United States Patent
Tomany et al.

(10) Patent No.: US 9,929,000 B2
(45) Date of Patent: Mar. 27, 2018

(54) METHOD AND AN APPARATUS FOR IONIZING A SAMPLE

(71) Applicant: Waters Technologies Corporation, Milford, MA (US)

(72) Inventors: Michael J. Tomany, North Grosvenor Dale, CT (US); Marc V. Gorenstein, Needham, MA (US); Joseph A. Jarrell, Newton Highlands, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 466 days.

(21) Appl. No.: 14/523,350

(22) Filed: Oct. 24, 2014

(65) Prior Publication Data

US 2015/0118762 A1    Apr. 30, 2015

Related U.S. Application Data

(60) Provisional application No. 61/895,484, filed on Oct. 25, 2013.

(51) Int. Cl.

| | |
|---|---|
| *H01J 49/00* | (2006.01) |
| *H01J 49/10* | (2006.01) |
| *H01J 49/14* | (2006.01) |
| *G01N 30/72* | (2006.01) |
| *G01N 33/68* | (2006.01) |
| *H01J 49/04* | (2006.01) |

(52) U.S. Cl.
CPC .............. *H01J 49/10* (2013.01); *G01N 30/72* (2013.01); *G01N 30/7266* (2013.01); *G01N 33/6848* (2013.01); *H01J 49/0445* (2013.01); *H01J 49/145* (2013.01); *Y10T 436/25875* (2015.01)

(58) Field of Classification Search
CPC ....................................................... H01J 49/10
USPC ............................................................ 436/181
See application file for complete search history.

(56) References Cited

U.S. PATENT DOCUMENTS

| | | | | |
|---|---|---|---|---|
| 4,977,785 | A | * | 12/1990 | Willoughby ........ H01J 49/0445 239/86 |
| 5,015,845 | A | * | 5/1991 | Allen ................ G01N 27/44717 250/281 |
| 6,147,347 | A | * | 11/2000 | Hirabayashi .......... H01J 49/045 204/452 |
| 8,232,521 | B2 | | 7/2012 | Jarrell et al. |

OTHER PUBLICATIONS

Kenzo Hiraoka, Konosuke Murata, Keiichi Aizawa, Fumiko Matsushita, Hiroko Fukasawa and Tetsuya Sato "Explosive Vaporization of a Liquid Water Beam by Irradiation with a 10.6 pm Infrared Laser" Rapid Communications in Mass Spectrometry, vol. 11, 474-478 (1997).*

K. K Hiraoka, H. Fukasawa, F. Matsushita and K. Aizawa "High-flow Liquid Chromatography/Mass Spectrometry Interface Using a Parallel Ion Spray" Rapid Communications in Mass Spectrometry, vol. 9, 1349-1355 (1995).*

* cited by examiner

*Primary Examiner* — Christopher Adam Hixson
*Assistant Examiner* — Emily R. Berkeley
(74) *Attorney, Agent, or Firm* — Schmeiser, Olsen & Watts LLP

(57) ABSTRACT

A method of ionizing a sample includes providing an aqueous liquid and directing a jet comprising carbon dioxide to interact with the provided aqueous liquid. One or both of the aqueous liquid and the jet comprise the sample. At least a portion of the sample is ionized due to the interaction.

9 Claims, 4 Drawing Sheets

METHOD AND AN APPARATUS FOR IONIZING A SAMPLE

CROSS-REFERENCE TO RELATED APPLICATION

This application claims priority to and benefit of U.S. Provisional Application No. 61/895,484 filed Oct. 25, 2013, which is incorporated herein by reference in its entirety.

TECHNICAL FIELD

This disclosure relates generally to ionizing a sample for mass spectrometric detection, without application of a voltage, and, more particularly, to ionizing a sample through the impact interaction of a jet formed from a liquid containing carbon dioxide, the sample and an aqueous liquid.

BACKGROUND

Mass spectrometry (MS) requires sample molecules to be converted into ions before mass analysis can be performed. There are a variety of ionization techniques used in MS, among which the most common include electron impact (EI), atmospheric pressure chemical ionization (APCI), atmospheric pressure photo ionization (APPI), matrix-assisted laser desorption/ionization (MALDI) and electrospray ionization (ESI).

EI only works for gas and volatile organic molecules, wherein thermally excited electrons interact with gas phase atoms or molecules to produce ions, and is coupled predominantly with gas chromatography (GC). EI, due to its high degree of fragmentation, is not suitable for bio-molecules, which tend to be fragile and easily fragmented. APCI works for both gas and liquid, in which ions are produced through the collision of sample molecules with ions of a reagent gas. APCI requires high temperatures, typically above 400° C., to convert a liquid sample into a gaseous state before the sample can be ionized by chemical ionization initiated by a corona discharge electrode. Hence, APCI, like EI, is not well suited for bio-molecules. APPI is similar to APCI except the chemical ionization is initiated by photons.

MALDI and ESI are soft ionization techniques and can be applied to a wide range of samples, including fragile bio-molecules, e.g., amino acids, peptides and proteins. MALDI entails samples dried on a surface so is not well suited as an online MS interface, e.g., for online ionization of a sample eluted from a liquid chromatography (LC) column. As a result, MALDI is normally not coupled with an online separation technique. ESI works for liquid samples and is regarded as an ideal interface to couple a LC module directly online to a mass spectrometer. Nonetheless, ESI requires a high voltage, typically in a range of 2 kV to 6 kV, to promote ionization and such a requirement is not only expensive but also hazardous. And both MALDI and ESI have difficulty with non-polar samples.

One technique for ionizing samples without application of a high voltage or high temperatures entails directing a jet, formed by emitting liquid carbon dioxide from an orifice, to a surface containing samples. Though such a technique involves no voltage nor high temperatures, it requires samples to be on or in a surface, and therefore is not well suited for directly coupling a LC module to a mass spectrometer.

SUMMARY

Some embodiments arise, in part, from the realization that a sample can be ionized for mass spectrometric detection, without application of a voltage, through the impact interaction of a jet formed from a liquid containing carbon dioxide, the sample and an aqueous liquid. The sample can be present in one or both of the aqueous liquid and the jet. For example, aqueous liquid is sprayed into the jet to interact therewith. Or, the aqueous liquid emerges via an outlet of an aqueous liquid source or is provided on a surface, and the jet is directed at the outlet or the surface to interact with the aqueous liquid. Or, the fluids, the sample and jet and aqueous liquid, are mixed and then sprays at a surface to promote ionization. Some embodiments control the jet to produce at least some frozen particles in the jet. In some embodiments, interaction of the jet with an aqueous spray promotes ionization. Some alternative embodiments mix carbon dioxide and aqueous-based fluids prior to forming the jet. The jet is then optionally directed at an impact surface on or proximate to the inlet of a MS module.

Some of these embodiments are interfaces that couple a LC module directly online to a MS module.

Some embodiments provide methods of ionizing a sample, which includes providing an aqueous liquid, and directing a jet including carbon dioxide to interact with the provided aqueous liquid, wherein one or both of the aqueous liquid and the jet comprise the sample, wherein at least a portion of the sample is ionized due to the interaction.

Optionally, the jet is formed from a fluid, and a temperature of the fluid is controlled to form a jet that contains frozen particles including carbon dioxide, wherein the controlled temperature is in a range of about minus 15° C. to about 15° C.

In some implementations, the aqueous liquid contains at least about 10% water by volume.

In some implementations, providing the aqueous liquid includes spraying the aqueous liquid, and the method further includes delivering a nebulizing gas to the sprayed liquid to substantially prevent freezing of water of the liquid, and directing the jet source toward the spray.

In other implementations, providing the aqueous liquid includes delivering the aqueous liquid via a supply component, and further including directing the jet source toward an outlet of the supply component.

In further implementations, the method further includes forming the jet from a fluid that is in a liquid, supercritical or near-supercritical state.

Another embodiment features an ionization device, which includes a liquid source configured to deliver a liquid via an outlet of the liquid source and a jet source configured to direct a jet including carbon dioxide to interact with at least a portion of the delivered liquid. One or both of the liquid and the jet contain the sample, and at least a portion of the sample is ionized due to the interaction of the fluid and the jet.

In some implementations, the jet source includes a fluid supply line, for delivering a fluid including carbon dioxide to form the jet, and a temperature control unit configured to control a temperature of the fluid in the supply line, whereby at least a portion of the jet contains frozen particles including carbon dioxide.

In some cases, the liquid contains water. In some of these cases, the liquid is at least about 10% water by volume.

In some cases, the jet source is directed toward the outlet of the liquid source.

In some cases, the liquid source is configured to spray the liquid from the outlet of the liquid source, wherein the jet source is directed toward the spray, and the liquid source includes a gas supply to assist nebulization of the sprayed liquid for substantially preventing freezing of water of the liquid.

In other cases, the jet source is disposed to direct the jet toward an inlet of a MS module.

In some cases, the jet source includes a fluid supply line that delivers a fluid in a liquid, supercritical or near-supercritical state. In many cases, the liquid source provides no applied voltage to the liquid exiting the outlet.

A further embodiment features a chemical-analysis apparatus, which includes an ionization device, including a liquid source configured to deliver a liquid via an outlet of the liquid source without application of a voltage, and a jet source configured to direct a jet including carbon dioxide to interact with at least a portion of the delivered liquid. One or both of the liquid and the jet contain the sample, and at least a portion of the sample is ionized due to the interaction of the fluid and the jet. The chemical-analysis apparatus further includes a chromatography module that supplies the liquid to the liquid source or a fluid to the jet source and a mass-spectrometry module that receives the ionized sample. The fluid comprises the carbon dioxide and is in a liquid, supercritical or near-supercritical state.

In some implementations, the chromatography module is configured to supply the liquid or the fluid at a flow rate of less than about 5 mL/min.

Other implementations, features and advantages will be apparent in view of the description, drawings and claims.

BRIEF DESCRIPTION OF THE DRAWINGS

In the drawings, same or like reference characters and numbers generally refer to same or like elements throughout different views. Also, the drawings are not necessarily to scale.

DETAILED DESCRIPTION

Some illustrative implementations will now be described with respect to FIGS. 1-3. In view of this description, claims and figures, modifications and alterations to these implementations, and alternative embodiments, will be apparent to one of ordinary skill.

Figure 1A:
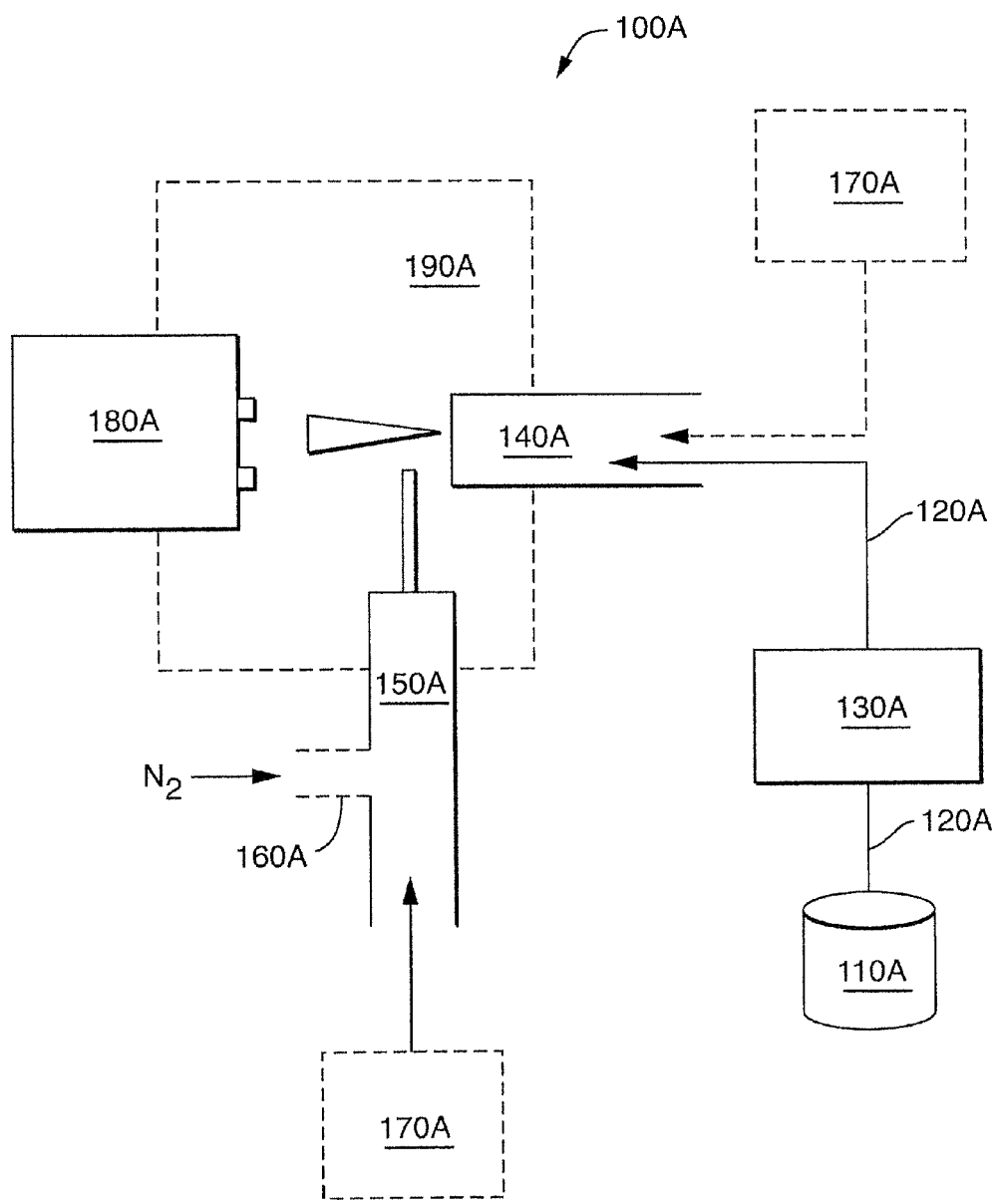
FIG. 1A is a schematic overview of an ionization device 100A, in accordance with one embodiment of the invention.

FIG. 1A is a schematic overview of an ionization device 100A for ionizing a sample, which includes a carbon dioxide source 110A, a fluid supply line 120A, a temperature control unit 130A, a jet source 140A, and a liquid source 150A. The device 100A also optionally includes nebulizing features, supported by a nebulizer inlet 160A, presented by dashed lines.

The carbon dioxide source 110A delivers a supercritical or near-supercritical fluid containing carbon dioxide to the jet source 140A through the fluid supply line 120A. The carbon dioxide source 110A can be, for example, a stainless steel tank pressurized at 1000 psi or higher, or an eluent supply line from a chromatography application.

The temperature control unit 130A can be anywhere along a path to the jet to control a temperature of fluid emitted from the jet source 140A. Preferably, the temperature is selected so that at least some amount of frozen particles including carbon dioxide is formed during expansion of the carbon-dioxide based fluid, to promote sample ionization. In some implementations, the temperature control unit 130A is disposed in the supply line 120A, between the carbon dioxide source 110A and the jet source 140A. Alternatively, the temperature control unit 130A can be attached to an exterior surface of the jet source 140A or placed anywhere along a path close to the carbon dioxide source 110A. The fluid is first directed to the temperature control unit 130A and the fluid having a controlled temperature is then directed to the jet source 140A. In some implementations, the temperature control unit 130A is a Peltier device, and the temperature is controlled to be in a range of about minus 15° C. to about 15° C.

The jet source 140A has an outlet, through which the carbon-dioxide based fluid expands into a state having a much lower pressure, e.g. an atmospheric pressure, to form a jet of the fluid. The jet includes gaseous carbon dioxide, liquid carbon dioxide droplets and/or frozen carbon dioxide particles. The jet cools upon expansion, and the cooling is sufficient to preferably produce an amount of frozen particles. The cooling phenomenon is an example of the Joule-Thomson effect. The temperature of the expanding jet can be varied, depending on, e.g., the pressure imposed on the jet, and can be as low as, e.g., about minus 78° C., at atmospheric pressure. In some implementations, the jet source 140A can be a capillary having an internal diameter in a range of about 10 um to about 60 um.

The liquid source 150A is configured to supply an aqueous liquid and to direct the aqueous liquid to intersect and interact with the jet. The liquid source 150A can be positioned at any angle to the jet source 140, so long as the aqueous liquid can intersect the jet. The aqueous liquid is at least about 10% water by volume and can also include an organic solvent, e.g., methanol, acetonitrile or the like, or a mixture thereof.

The sample can be in one or both of the aqueous liquid and the fluid supplied to the jet source 140A. At least a portion of the sample is ionized due to the interaction of the aqueous liquid and the jet.

In some implementations, the sample is injected to the aqueous liquid, which carries the sample to intersect the jet of the carbon-dioxide based fluid. In other implementations, the sample can be mixed with liquid carbon dioxide prior to forming the jet. In further implementations, the sample can be injected into both the aqueous liquid and the jet of the fluid. Or, the sample can be carried in an eluent from a chromatography device or carried by a nebulizer gas.

The sample can be simple or complex, and soluble or insoluble in water. One example of a complex sample is lipids which are insoluble in water.

As mentioned, the device 100A can include a nebulizer to convert a sample containing liquid into a mist of droplets before sample ionization to prevent or reduce formation of water ice. The nebulizer can be a pneumatic nebulizer using nitrogen gas as a nebulizer gas.

A sprayer can also optionally be added to the device 100A to spray water to the intersection between the jet of the carbon dioxide and the liquid delivered from the liquid source 150A. The sprayer can be a nozzle-like element.

The device 100A further includes a chromatography module 170A and a mass spectrometer 180A, and optionally includes an ion enclosure 190A, presented by a dashed line box.

The chromatography module 170A, e.g., a LC module, supplies a liquid to the liquid source 150A, wherein the liquid carries samples eluted from or separated by the chromatography module 170A and contains a portion of water. Alternatively, water from a separate source can be added to the liquid, eluted from the chromatography module 170A. The chromatography module 170A is preferably configured to deliver the liquid at a flow rate of less than about 5 mL/min.

If the flow rate delivered by the chromatography module 170A is low enough, then addition of a nebulizer is unnecessary, as the expanding jet of the carbon dioxide can function as a nebulizer to promote formation of droplets. However, if the flow rate is high, then additional mechanical gas from a nebulizer is desirable to nebulize the flow from the chromatography module 170A.

Alternatively, the device 100A includes a chromatography module 170A that connects to the jet source 140A to supply a fluid containing carbon dioxide, in a liquid, supercritical or near-supercritical state. In such an implementation, a sample can be carried by either the liquid from the liquid source 150A or by the fluid from the chromatography module 170A, or both, and ionized through the intersection between the jet and the liquid. The mass-spectrometry module 180A receives the ionized sample for mass analysis.

Figure 1B:
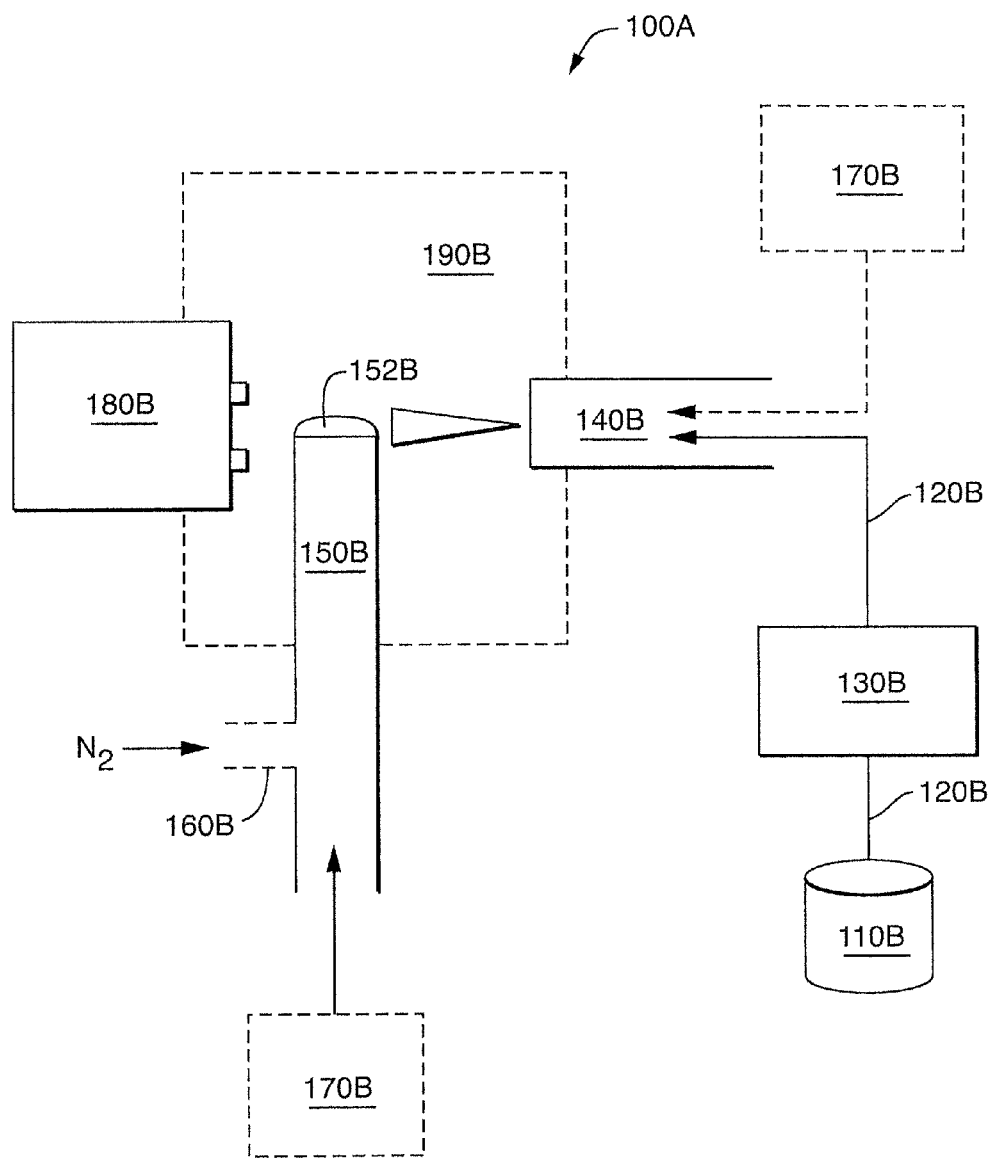
FIG. 1B is a schematic overview of an ionization device 100B, in accordance with another embodiment of the invention.

Alternatively, as shown in FIG. 1B, the aqueous liquid, instead of being sprayed into the jet, emerges via an outlet 152B of the liquid source 150B, and the jet is directed at the outlet 152B to interact with the aqueous liquid.

Figure 2A:
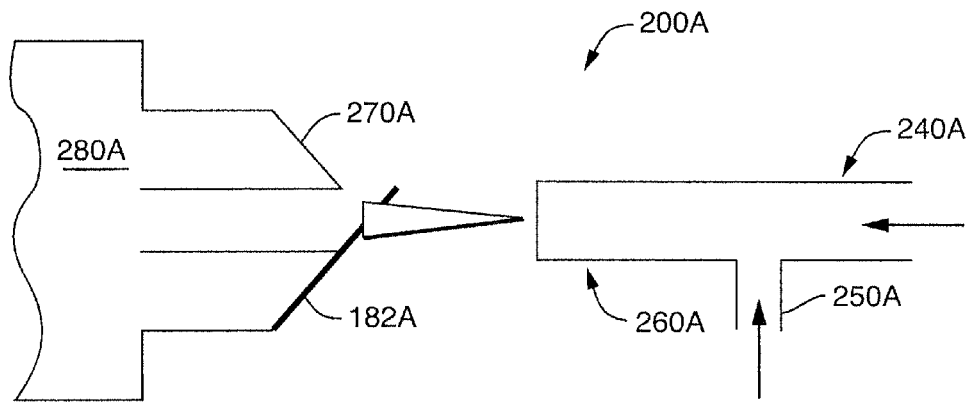
FIGS. 2A and 2B are schematic views of alternative configurations of ionization devices 200A and 200B, in accordance with some embodiments of the invention.
Figure 2B:
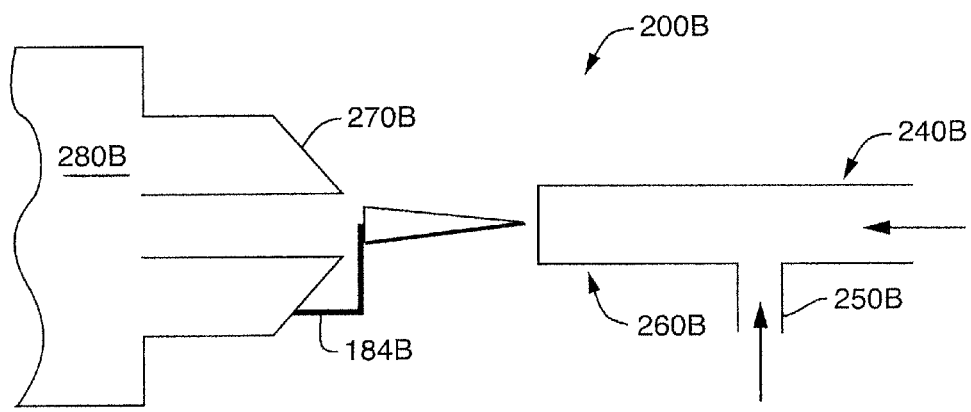

FIGS. 2A and 2B are schematic views of two alternative embodiments of an apparatus 200A, 200B. The apparatus 200A includes a MS module 280A having an entrance 270A, a liquid delivery conduit 250A, a carbon dioxide delivery conduit 240A and a jet source 260A. The conduits 240A, 250A are joined to mix the liquid and carbon dioxide and deliver the mixture to the jet source 260A. The apparatus 200A also includes a spray target having a flat surface 182A, which is disposed at the entrance 270A of the MS module 280A. The spray target is positioned such that the flat surface 182A can intersect the jet emitted from the jet source 140A but does not block the entrance 270A. The jet can impact on the surface 182A, whereby at least a portion of the sample is ionized due to the impact, and the ionized sample can enter the MS module 280A for further mass detection and analysis.

In contrast to the apparatus 100A, 100B, carbon dioxide and liquid are mixed prior to forming a jet, and the jet impacts a surface to promote ionization. The sample can be in one or both of the liquid and carbon dioxide before mixing, and at least a portion of the sample is ionized due to the impact of the jet on the surface. In the configuration shown in FIG. 2A, the jet impacts on the flat surface 182A, while in the configuration of FIG. 2B, the jet impacts on a stainless steel wire 184B attached to the entrance 270B of a mass spectrometer 280B. The wire 184B is positioned such that the jet can impact thereon and a portion of the sample is ionized as a result, and the ionized sample can enter the MS module 280B to be further analyzed.

Figure 3:
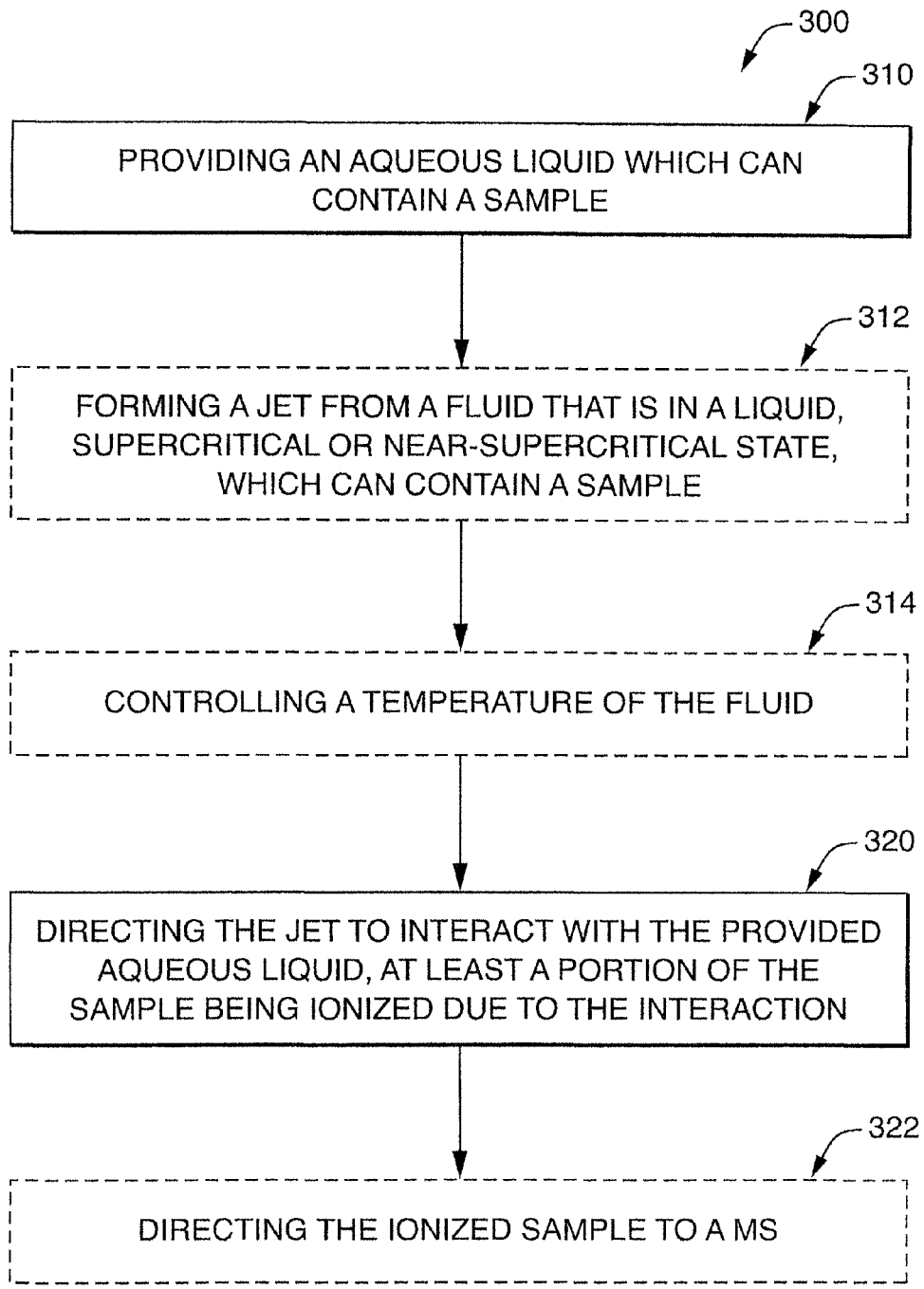
FIG. 3 is a flow diagram of a method of ionizing a sample, in accordance with one embodiment of the invention.

FIG. 3 is a flow chart of a method 300 of ionizing a sample for mass spectrometric detection without application of a voltage, and, more particularly, to ionizing a sample through the impact interaction of a jet, formed from a liquid containing carbon dioxide, the sample and an aqueous liquid. The sample can be present in one or both of the aqueous liquid and the jet. The method includes providing (310) an aqueous liquid and directing (320) a jet including carbon dioxide to interact with the provided aqueous liquid. One or both of the aqueous liquid and the jet contain the sample, and at least a portion of the sample is ionized due to the interaction.

The method 300 optionally includes forming (312) the jet from a fluid that is in a liquid, supercritical or near-supercritical state and controlling (314) a temperature of the fluid before forming a jet such that at least some frozen particles including solid carbon dioxide are formed during expansion of the carbon dioxide. In some implementations, controlling (314) the temperature involves a Peltier device, and the temperature is selected to have a value in a range of about minus 15° C. to about 15° C.

The step of providing (310) optionally includes spraying water or liquid containing at least about 10% water by volume, to intersect the jet. In addition, providing (310) can include supplying a liquid containing a sample eluted from a chromatography module, and providing (310) can further include nebulizing the liquid from the chromatography module into a mist of droplets.

The method 300 can further include directing (322) the ionized sample toward an inlet of a mass-spectrometry module for mass detection and analysis. The steps (312, 314 and 322) enclosed in dashed-line boxes are alternative or optional steps of the claimed method.

The method can ionize samples without application of a voltage or/and high temperatures and be applied to a wide range of samples, including fragile bio-molecules, e.g., amino acids, peptides and proteins, and is particularly good for analysis of lipids, which are insoluble in water.

Although a number of implementations have been described above, other modifications, variations and implementations are possible in light of the foregoing teaching. For example, though, as described above, the carbon dioxide source 110 can be a stainless steel tank pressurized at 1000 psi or higher, it can be an eluent supply line from a supercritical fluid chromatography (SFC) system. In such implementations, the SFC system can be both a sample and carbon dioxide source, where a sample is eluted with carbon dioxide, in a SFC mobile phase, which optionally includes a modifier, and is directed to interact with an aqueous liquid.

For example, though, as described above, methods generally apply to samples in an aqueous liquid stream, the liquid can apply to samples on or in a surface.

What is claimed is:

1. A method of ionizing a sample, comprising:
generating a spray of an aqueous liquid comprising a sample; and
directing a jet comprising frozen particles of carbon dioxide toward the spray such that the frozen particles of carbon dioxide interact with the aqueous liquid, wherein at least a portion of the sample is ionized due to the interaction.

2. The method of claim 1, wherein the jet is formed from a fluid, the method further comprising controlling a temperature of the fluid.

3. The method of claim 2, wherein the controlled temperature is in a range of about minus 15° C. to about 15° C.

4. The method of claim 1, wherein the aqueous liquid comprises at least 10% water by volume.

5. The method of claim 1, further comprising delivering a nebulizing gas to the spray of the aqueous liquid to prevent freezing of water in the liquid.

6. The method of claim 2, further comprising forming the jet from a fluid that is in a liquid, supercritical or near-supercritical state.

7. The method of claim 1 wherein the spray of the aqueous liquid is in a first direction and the jet comprising frozen particles of carbon dioxide is in a second direction that is different from the first direction.

8. The method of claim 1 wherein the aqueous liquid comprises at least one of methanol and acetonitrile.

9. The method of claim 1 wherein generating the spray of the aqueous liquid comprises supplying a flow of a nebulizer gas to a source of the aqueous liquid.

* * * * *